United States Patent [19]
Johnson et al.

[11] Patent Number: 6,114,157
[45] Date of Patent: Sep. 5, 2000

[54] METHOD FOR INCREASING TOTAL PRODUCTION OF 4-HYDROXYBENZOIC ACID BY BIOFERMENTATION

[75] Inventors: Bruce Fletcher Johnson, Scotia; Mohan Amaratunga, Clifton Park; John Henry Lobos, Ballston Spa, all of N.Y.

[73] Assignee: General Electric Company, Schenectady, N.Y.

[21] Appl. No.: 09/161,129

[22] Filed: Sep. 25, 1998

[51] Int. Cl.⁷ .................. C12P 7/42; C12N 1/20
[52] U.S. Cl. .......... 435/146; 435/252.33; 435/252.8; 435/949
[58] Field of Search ............... 435/146, 252.33, 435/252.8, 849

[56] References Cited

U.S. PATENT DOCUMENTS 4,851,573   7/1989   Kulprathipanja et al. ............. 562/580

FOREIGN PATENT DOCUMENTS 28 52 596    6/1979   Germany.
44-002456B   1/1969   Japan.
1111310      4/1968   United Kingdom.

OTHER PUBLICATIONS

W. Crueger and A. Crueger, Biotechnology: A Textbook of Industrial Microbiology, Sinauer Associates, Sunderland, MA, pp. 124–174 (1990).

B. Atkinson and F. Mavituna, Biochemical Engineering and Biotechnology Handbook, second edition, Stockton Press, NY, pp. 243–364 (1991).

A. Berry, Tibtech 14:250–256 (1996).

P. Vonktaveesuk et al., J. Ferment. Technol. 77:508–512 (1994).

Y. Nomura et al., J. Ferment. Technol. 71:450–452 (1991).

V. Yabannavar and D. Wang, Biotechnol. Bioeng. 37:1095–1100 (1991).

S. Zhang and K. Toda, J. Ferment. Technol. 77:288–292 (1994).

B. Atkinson and F. Mavituna, Biochemical Engineering and Biotechnology Handbook, second edition, Stockton Press, NY, pp. 905–1022 (1991).

*Primary Examiner*—Herbert J. Lilling
*Attorney, Agent, or Firm*—Mike W. Crosby; Noreen C. Johnson

[57] ABSTRACT

This invention pertains to a method of production of 4-hydroxybenzoic acid, with purification and recovery of 4-hydroxybenzoic acid directly from the fermentation medium of a cultured organism, in the presence of other chemical species. Ion exchange resin is used during the fermentation process to recover the chemical product without the necessity of separating the biomass from the fermentation supernatant by filtration after fermentation is complete and then treating the filtrate to recover the product. This reduces or eliminates the need for filtration steps and eliminates the need for energy-intensive water removal processes. Furthermore, the removal of the product during the fermentation dramatically increases the production of the product during the fermentation process. This method therefore can both increase the amount of product produced in a single fermentation run and reduce the per unit cost of its biocatalytic production.

8 Claims, 3 Drawing Sheets

METHOD FOR INCREASING TOTAL PRODUCTION OF 4-HYDROXYBENZOIC ACID BY BIOFERMENTATION

This invention was made with Government support under Government Contract No. 70NANB5H1135, awarded by the National Institute of Science and Technology. The Government has certain rights in this invention.

TECHNICAL FIELD

This invention relates to a method for producing 4-hydroxybenzoic acid (parahydroxybenzoic acid, PHB) using biofermentation. This method increases the potential total production of PHB and recovery of PHB from the fermentation medium. In particular, the invention is directed toward a method for removing PHB from a fermentation mixture by continuous exposure and binding to an anion exchange resin during its biocatalytic production.

BACKGROUND ART

Organic synthesis of chemical intermediates and raw materials important to the polymer and chemical industries can be a major portion of the cost of production of the finished product made from them. Often, starting materials are synthesized from petroleum products which are non-renewable, expensive, and may be hazardous. In addition, the cost of petroleum products is dependent on world markets and other factors which can not be controlled. Another factor which increases costs in the production of organic molecules by a chemical synthetic route is the resulting waste stream of unwanted byproducts and contaminated solvents, the disposal of which is expensive and hazardous. Yet, for most chemical starting materials and intermediates, there is no other practical alternative to chemical synthesis.

Production of starting materials by biofermentation is an alternative which uses renewable resources and creates much less hazardous waste. The fermentative production of a few chemicals has been reported (W. Crueger and A. Crueger, *Biotechnology: A Textbook of Industrial Microbiology*, Sinauer Associates, Sunderland, Mass., pp. 124–174 (1990); B. Atkinson and F. Mavituna, *Biochemical Engineering and Biotechnology Handbook*, second edition, Stockton Press, NY, pp. 243–364 (1991)) and commercialized. In a recent review on improving the production of aromatic compounds in *Escherichia coli* (*E. coli*) by metabolic engineering, an extensive array of compounds is detailed (A. Berry, Tibtech 14:250–256 (1996)).

Unfortunately, this is not a commercially feasible alternative for a great many desirable molecules because the molecule of interest is produced in such small amounts by the biocatalytic organisms. Even organisms genetically engineered to produce enhanced amounts of the desired molecule often do not produce concentrations of the product great enough to justify the investments necessary to develop a commercial biofermentation process. This can be particularly true when the product is toxic to the cells or is regulated by a negative feedback mechanism, thereby limiting the potential concentration of the product in the fermentation medium.

At the same time, one of the greatest challenges to the development of a biofermentative process is the separation, recovery, and purification of the product from the fermentation medium at relatively low concentrations and in the presence of other chemical species. Removal of the desired metabolites from fermentation mixtures is typically performed after the termination of the fermentation process. Generally, the process involves a first filtration step to separate the biomass and yield a clarified solution from which product is removed. Often, the process then includes an energy-intensive water-removal step to concentrate the desired product or products. The product of interest must then be separated from the other molecules in the fermentation medium, for example metabolic byproducts and culture medium constituents.

This separation and purification may be performed by any of a number of techniques known in the art of biochemistry, such as electrodialysis, electrophoresis, sedimentation, solvent extraction, precipitation, or distillation. For example, lactic acid may be purified from fermentation medium using electrodialysis (P. Vonktaveesuk et al., J. Ferment. Technol. 77:508–512 (1994); Y. Nomura et al., J. Ferment. Technol. 71:450–452 (1991) or extraction (V. Yabannavar and D. Wang, Biotechnol. Bioeng. 37:1095–1100 (1991)). Acetic acid has also been purified after biofermentation using electrodialysis (S. Shang and K. Toda, J. Ferment. Technol. 77:288–292 (1994)).

Standard techniques are not commercially viable unless the product is present in the fermentation broth in relatively high concentrations, therefore they are limited in usefulness to products which are produced in relatively high concentrations in the fermentation medium. Even when feasible to do in the laboratory, the product recovery steps add to manufacturing costs often preventing the commercialization of the fermentative production of a wide range of chemicals. For production of these compounds to be cost-effective, more selective and less expensive techniques must be developed to remove and purify low concentrations of product.

For example, 4-hydroxybenzoic acid (PHB), a key monomer in the synthesis of liquid crystalline polymers (LCPs) with additional utility as a chemical intermediate for the manufacture of paraben preservatives and other products, is currently produced by organic chemical synthesis and costs approximately $2.40/lb. The high cost of PHB contributes significantly to the high cost of LCPs and thus limits the applications to which LCPs can be put commercially. The biofermentative production of PHB from glucose can potentially reduce the manufacturing costs of LCPs now, and in the future by insulating PHB from potential increasing petrochemical costs as oil reserves are depleted. A key challenge in the fermentative production of this chemical, however, is the isolation of the desired product from the aqueous fermentation mixture at relatively low concentrations (<10% w/v) in the presence of other chemical species (W. Crueger and A. Crueger, *Biotechnology: A Textbook of Industrial Microbiology*, Sinauer Associates, Sunderland, Mass., pp. 111–123 (1990); B. Atkinson and F. Mavituna, *Biochemical Engineering and Biotechnology Handbook*, second edition, Stockton Press, NY, pp. 905–1022 (1991)).

PHB can be made from glucose using *E. coli*, which produces the chemical as a minor metabolite and excretes the product into the medium at levels of less than 2 mg/L. The biosynthetic pathway in *E. coli* is shown in FIG. 1. A significant number of steps are required in the metabolic pathway from 3-deoxy-D-arabino-heptulosonate-7-phosphate (DAHP) to chorismic acid, variously termed the chorismic acid, aromatic amino acid, or shikimic acid pathway.

Genetically engineered biocatalysts are known to produce chemicals like PHB. However, the amounts produced by these strains are not optimal for recovery by the prior art methods. There is a need, therefore, for a method to increase the recovery of PHB commercially produced using biofermentative methods.

SUMMARY OF THE INVENTION

Accordingly, this invention provides a method for producing 4-hydroxybenzoic acid by biofermentation comprising providing a culture of biocatalyst which produces 4-hydroxybenzoic acid in a fermentation medium; allowing the biocatalyst to produce 4-hydroxybenzoic acid by fermentation; removing 4-hydroxybenzoic acid from the fermentation during at least a portion of the fermentation by passing the fermentation medium through an anion exchange resin which binds 4-hydroxybenzoic acid for at least a portion of the biofermentation; and extracting the anion exchange resin to remove bound 4-hydroxybenzoic acid. This results in superior recovery of the product and higher production of the product by the biocatalyst.

DESCRIPTION OF THE INVENTION

Figure 1:
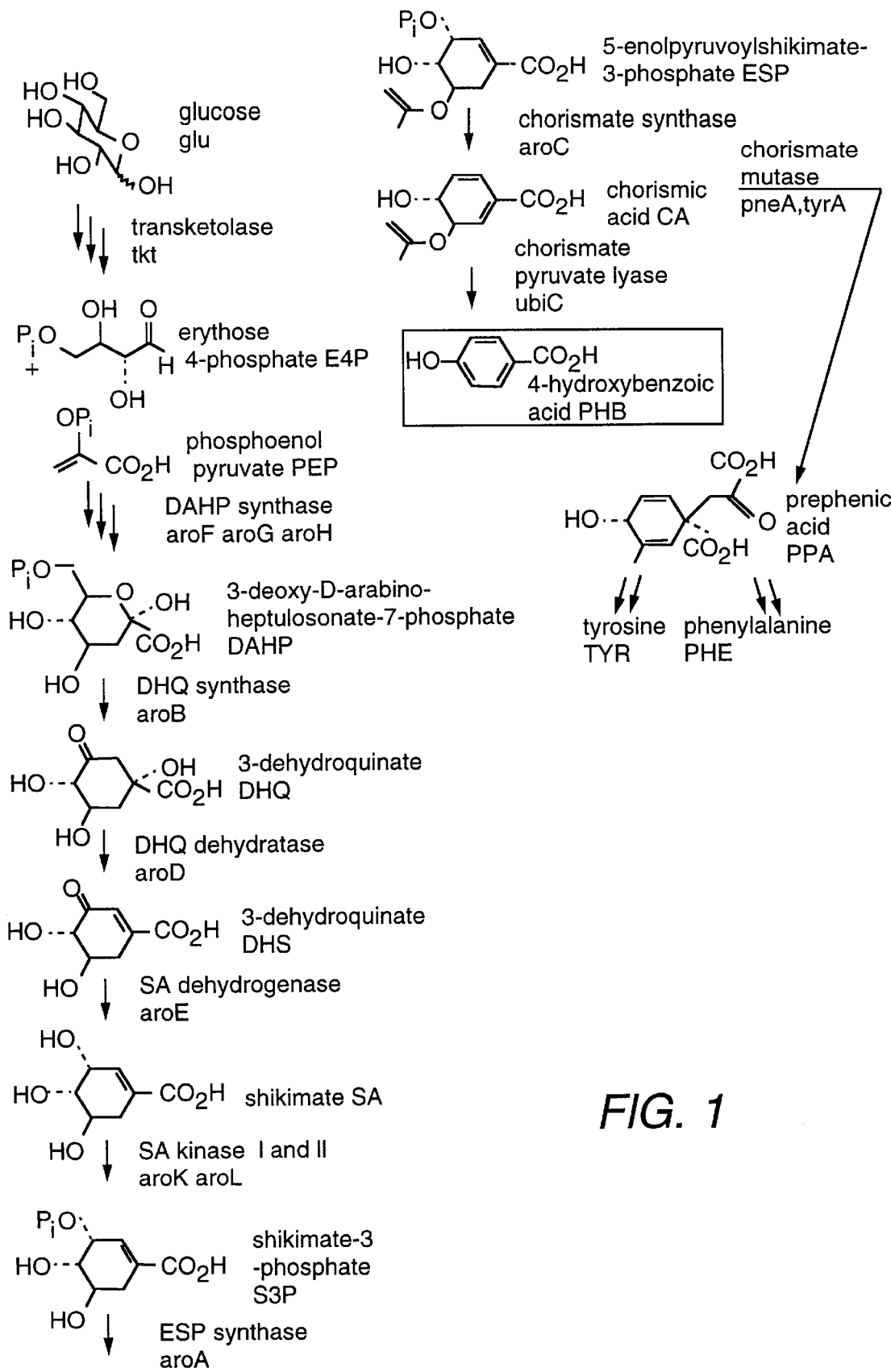
FIG. 1 is a schematic diagram showing the biosynthetic pathway for the production of chorismate, PHB and aromatic amino acids from glucose in *E. coli.*

According to the method of the invention, the biocatalysis product, PHB is continuously removed during at least part of the fermentation process. Biocatalysis may be performed by any fermentation method available in the prior art, using any cell capable of producing the molecule. Wild type or genetically engineered cells may be used with this method, for example an *E. coli* strain such as JP01B/pMCP2, a genetically engineered *E. coli* strain containing the multicopy plasmid pMCP2 which overproduces chorismic acid. Fermentation is desirably carried out in a fermentor, or any suitable container such as shake flask, using any medium which provides the correct nutritional support and sufficient raw materials for production of the desired final product.

A viable sample of JP01B *Escherichia coli* bacteria containing the pMCP2 multicopy plasmid was deposited with the American Type Culture Collection, 10801 University Boulevard, Manassas, VA 20110-2209 U.S.A., on May 10, 2000, under the terms of the Budapest Treaty and will be maintained for a period of thirty (30) years from the date of deposit, or for (5) years after the last request for the deposit, or for the enforceable period of the U.S. patent, whichever is longer. The deposit accession number is PTA-1857. The deposit is provided for convenience only, and is not required to practice the present invention in view of the teachings provided herein.

Anion exchange resin may be prepared by conversion to the phosphate form by prewashing with phosphate buffer and sterilization, for example by autoclaving or rinsing with alcohol. The resin is preferably placed in a separatory flask or funnel to minimize loss of the resin from the column to the stirred fermentor, but may be placed in any suitable column or other container. During at least part of a fermentation process, the fermentation medium is passed through the bed of anion exchange beads, preferably in an upwards direction, and back into the fermentor. The passage of culture medium through the beads may be performed during any portion of the fermentation process, preferably from 6 hours after addition of yeast to the reactor until the end of the fermentation process. The culture medium also may be passed through the beads throughout the entire fermentation process. The fermentation mixture is preferably pumped through the resin bed using a peristaltic pump to minimize cell disruption, but any suitable pump may be used. As the anion exchange beads become saturated with PHB during the fermentation, replacement with fresh beads or the initial use of a greater quantity of beads will further improve the production and removal of PHB from the medium.

The anion exchange resin for use with this invention may be a weakly basic or strongly basic type resin. If a weakly basic resin is used, the fermentation medium is desirably adequately acidic to protonate the basic group on the resin, for example about pH 7 to protonate a tertiary amine. Preferably, the anion exchange resin is a strongly basic cross-linked polystyrene-based resin such as IRA-400 (Amberlite®). The beads used with this invention desirably should have about 0.3 mmols to about 1.3 mmols cationic binding sites per mL fermentation medium, and preferably about 0.6 mmols to about 0.9 mmoles cationic binding sites per mL fermentation medium.

During fermentation, PHB becomes bound to the ion exchange resin as it is passed through the anion exchange beads, and fermentation medium depleted of PHB is returned to the fermentor. The concentration of PHB in the fermentor, thereby rapidly decreases once circulation through the anion exchange resin begins, and increases more slowly over the course of the fermentation process than in fermentations performed without exposure to anion exchange beads.

Once fermentation is completed, or once saturated anion exchange beads are removed from the system and replaced, the PHB is preferably recovered from the resin by extracting with acidic ethanol or sodium chloride in a water/ethanol mixture. Any pH, salt or chaotrope treatment which conveniently releases the PHB from the beads may be used. Anion exchange resin may be reused after the PHB is unbound, by first washing with phosphate buffer and resterilizing.

The following provide examples of fermentative processes to illustrate the invention, and are not intended to be limiting.

Anion exchange resin, IRA-400(CI) was converted to the phosphate form by washing the resin with 10 times the resin bed volume of 100 mM phosphate buffer, pH 7. Binding of PHB to the resin was performed in vials containing 1 ml basic culture medium (1 mM $MgSO_4$, 22 mM $KH_2PO_4$, 69 mM $K_2HPO_4$, 33 mM NaCl, and 39 mM $(NH_4)_2SO_4$), with 3.2 mM PHB, 3.7 mM tyrosine, and 3.5 mM phenylalanine. One set of vials also contained 1 ml bed volume of anion exchange resin, phosphate form (equivalent to 1.4 mmoles cationic sites), and one set also contained the anion exchange resin as above plus 7.4 mM sodium acetate. The total volume of all vials was brought to 10 ml with basic culture medium. The vials were shaken for 3 hours, then rested to allow the beads to settle. The supernatant was analyzed by HPLC to determine the amount of PHB, tyrosine, and phenylalanine remaining in solution.

Figure 2:
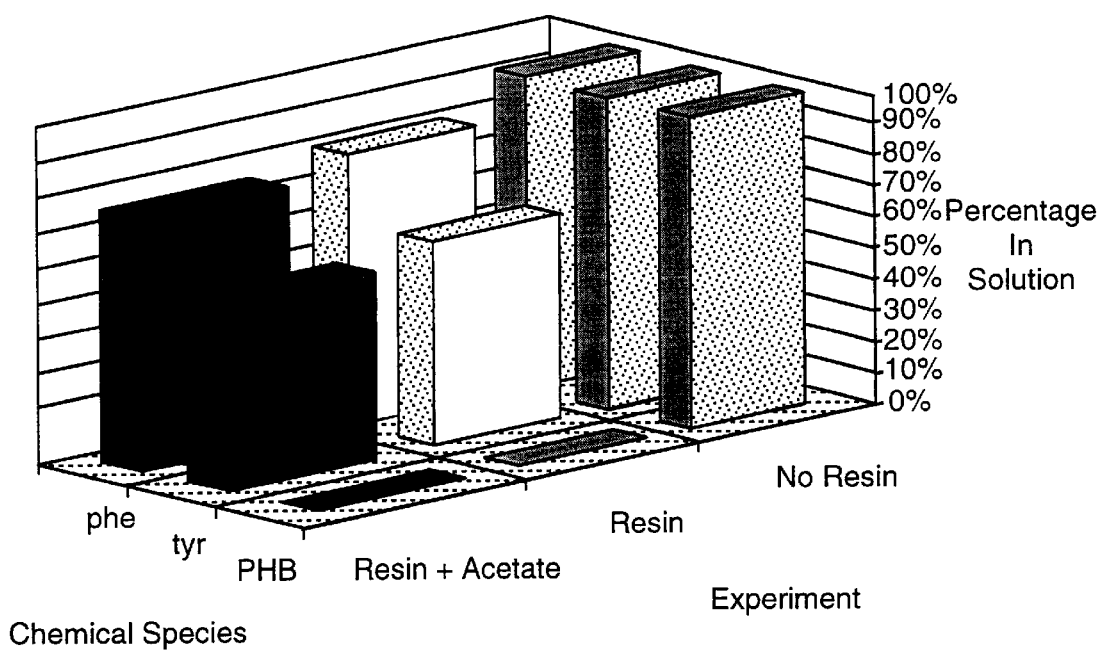
FIG. 2 depicts the binding of PHB, phenylalanine, and tyrosine to anion exchange resin in minimal culture medium in the presence of the competing amino acids and in the presence or absence of 7.4 mM acetate.

The results are shown in FIG. 2. In the absence of anion exchange resin, nearly 100% of the PHB recovered was in solution. In the presence of resin, however, over 97% of the PHB originally present in solution was bound. Only 30% and 15% of tyrosine and phenylalanine respectively was bound to the resin, demonstrating a high degree of specificity under the conditions tested. Even in the presence of excess competing anionic species (acetate ion), the anion exchange resin effectively adsorbed PHB, binding over 97% of the PHB in solution. This demonstrates the efficacy of this resin for the adsorption of PHB from aqueous solutions, even at low PHB concentration (3.2 mM).

Using this method, other ion exchange resins may be tested for the ability to specifically bind PHB under the fermentation conditions under which it will be produced.

2. Enhanced Fermentative Production of PHB.

Fermentative production of PHB was demonstrated in fermentors using the biocatalyst JP01B/pMCP2. JP01B is a strain of *E. coli* genetically engineered to overproduce chorismic acid. pMCP2 is a multicopy plasmid designed to overproduce ubiC, the gene coding for *E. coli* chorismate pyruvate lyase, the enzyme that converts chorismic acid to PHB.

Inocula for the fermentations were revived from frozen culture stock stored at −80° C. in 30% glycerol. The cultures were grown in 5 ml tubes of Luria broth containing 100 mg/L carbenicillin for 8 h before transferring a 1% volume into a 1 liter baffled shake flask containing 300 ml SMM medium (10 g/L glucose; 12.0 g/L $K_2HPO_4$; 3.0 g/L $KH_2PO_4$; 1.0 g/L $MgCl_2.6H_2O$; 4 g/L $(NH_4)_2SO_4$; 0.5 g/L $CaCl_2.2H_2O$; 0.4 mg/L $CuS_4O.5H_2O$; 0.5 mg/L $ZnSO_4.7H_2O$; 25.0 mg/L $MnSO_4.H_2O$; 1.0 mg/L $CoCl_2.6H_2O$; 0.2 mg/L sodium molybdate; 50 mg/L $FeSO_4.7H_2O$; 50 mg/L sodium citrate; 100 mg/L carbenicillin; and 1.0 g/L Amberex® 695 yeast extract). The baffled shake flasks were incubated 37° C. with vigorous shaking (300 rpm) for 15 hours before addition to the fermentors.

Each fermentor contained an initial volume of 3.5 liters of SMM medium before inoculating with 300 ml of an overnight culture of *E. coli* JP01B containing the pMCP2 plasmid. Carbenicillin (100 mg/L) was added to the medium initially to maintain cells containing the ampicillin resistance gene which is present on the pMCP2 plasmid. The initial glucose concentration was 0.5% (w/v). During fermentation, glucose was added using the DO-Stat method (K. Konstantinov et al.; Biotechnol. Bioeng. 36:750–758 (1990)) to control the rate of feeding. The dissolved oxygen (DO) was set at 20% of saturation (about 2 ppm $O_2$) by sparging with air. As the DO increased above the set point, the glucose feed increased to bring it back to 20%, and when the DO dropped below the set point, glucose feeding was reduced. The cultures were kept at 35° C., and the pH was controlled at 7.0 with $NH_4OH$ and $H_2SO_4$. The cultures were continuously agitated at 1000 rpm. Fermentations were run simultaneously under nearly identical conditions for over 50 hours.

One fermentation employed a culture recycle through Amberlite® IRA- 400(Cl) anion exchange resin for the continuous removal of PHB during biocatalyst growth and PHB production. The other did not. For the fermentation employing beads, beginning after the initial 5 hours of growth, the culture was continuously circulated through a 2 L conical funnel containing a 500 ml bed volume of anion exchange resin. The anion exchange resin had been converted to the phosphate form by washing with 10 times the resin bed volume of 100 mM phosphate buffer, pH 7 and sterilized with an ethanol rinse, followed by a sterile water rinse to remove the ethanol. The culture was pumped from the fermentor up through the bottom of the funnel at a rate of 400 ml/min to create a fluidized bed of the beads. The beads settled out of the top 1–2 inches of the culture medium in the bead reactor (funnel), creating an essentially bead-free culture medium supernatant. This culture medium was continuously returned to the fermentor. At the pumping rate employed, the entire culture volume was cycled through the beads every 10 minutes. After the fermentation was complete, the cell culture medium was rinsed off the beads with water before the beads were extracted to recover the PHB. The PHB was quantitatively recovered from the IRA-400 resin by soxhlet extraction using 3 L 95% ethanol containing one molar equivalent of trifluoroacetic acid. PHB concentration in the fermentation supernatants was determined by HPLC.

Figure 3:
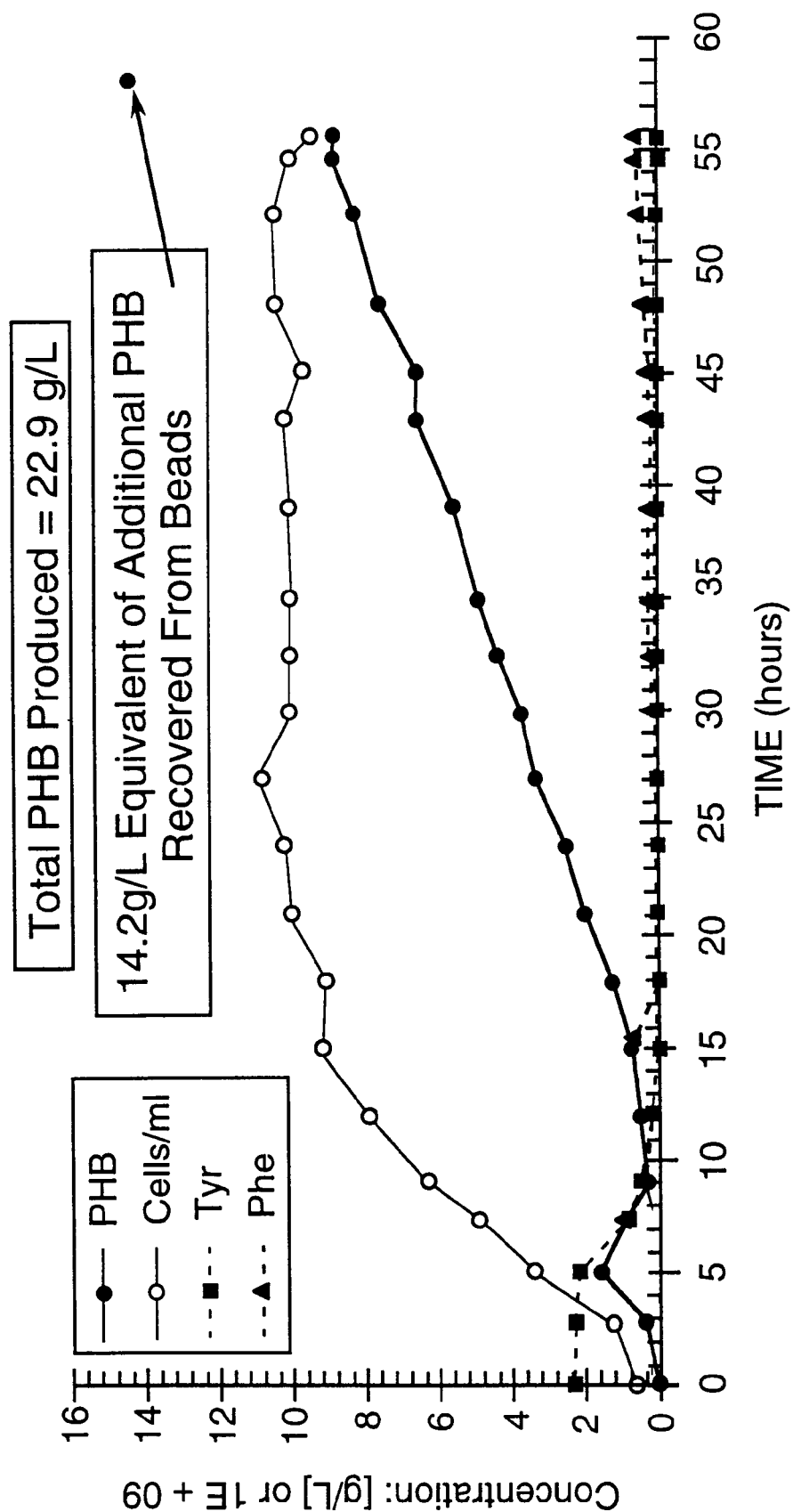
FIG. 3 shows the PHB, tyrosine, and phenylalanine produced during a biofermentation in the presence of anion exchange beads.

Results of the fermentation using beads according to the invention are reproduced in FIG. 3. The PHB recovered from the resin at the end of the fermentation was normalized to the final fermentation volume and is reported as a single data point (14.2 g/L). The concentration of PHB in the medium of the fermentation employing anion exchange beads after 55 hours of fermentation was 8.7 g/L, for a total equivalent recovery of 22.9 g/L (see FIG. 3). The best fermentation run under similar conditions without anion exchange resin produced 6 g/L PHB in the fermentation medium (data not shown).

What is claimed is:

1. A method for producing 4-hydroxybenzoic acid by biofermentation, comprising:

a) providing a culture of biocatalyst which produces 4-hydroxybenzoic acid in a fermentation medium;

b) allowing the biocatalyst to produce 4-hydroxybenzoic acid by fermentation;

c) removing 4-hydroxybenzoic acid from the fermentation medium by continuously passing the fermentation medium through an anion exchange resin which binds 4-hydroxybenzoic acid for at least a portion of the biofermentation; and d) extracting the anion exchange resin to remove bound 4-hydroxybenozic acid.

2. A method according to claim 1, wherein the biocatalyst is *E. coli.*

3. A method according to claim 2, wherein the *E. coli* is wild-type *E. coli.*

4. A method according to claim 2, wherein the *E. coli* is genetically engineered *E. coli.*

5. A method according to claim 4, wherein the *E. coli* is JP01B/pMCP2.

6. A method according to claim 1, wherein the fermentation medium is passed through the anion exchange resin using a peristaltic pump.

7. A method according to claim 1, wherein the direction of flow of the fermentative medium through the anion exchange medium is in an upward direction.

8. A method according to claim 1, wherein the anion exchange resin is contained in a conical-shaped container.

* * * * *